(12) United States Patent
Potter et al.

(10) Patent No.: US 11,083,636 B2
(45) Date of Patent: Aug. 10, 2021

(54) INCONTINENCE DETECTION SYSTEM CAPABLE OF IDENTIFYING URINARY OR FECAL INCONTINENCE

(71) Applicant: Hill-Rom Services, Inc., Batesville, IN (US)

(72) Inventors: Victor Potter, Middletown, OH (US); Neal Wiggermann, Batesville, IN (US); Gavin M. Monson, Oxford, OH (US); Dan R. Tallent, Hope, IN (US); Charles A. Lachenbruch, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 381 days.

(21) Appl. No.: 15/938,801

(22) Filed: Mar. 28, 2018

(65) Prior Publication Data

US 2018/0311080 A1 Nov. 1, 2018

Related U.S. Application Data

(60) Provisional application No. 62/491,466, filed on Apr. 28, 2017.

(51) Int. Cl.
*G08B 21/00* (2006.01)
*A61F 13/42* (2006.01)
(Continued)

(52) U.S. Cl.
CPC .............. *A61F 13/42* (2013.01); *A61B 5/002* (2013.01); *A61B 5/202* (2013.01); *A61B 5/4255* (2013.01); *A61B 5/7282* (2013.01); *A61B 5/746* (2013.01); *A61B 10/00* (2013.01); *A61B 90/98* (2016.02); *A61F 5/485* (2013.01); *A61G 12/00* (2013.01);
(Continued)

(58) Field of Classification Search
CPC ......... A61B 10/00; A61B 5/002; A61B 5/202; A61B 5/4255; A61B 5/7282; A61B 5/746; A61B 90/98; A61B 2562/029; A61B 2010/0083; A61F 13/42; A61F 5/485; A61F 2013/15056; A61F 2013/424; A61F 2013/8482; A61F 2013/15154;
(Continued)

(56) References Cited

U.S. PATENT DOCUMENTS 5,537,095 A 7/1996 Dick et al.
5,709,222 A 1/1998 Davallou
(Continued)

*Primary Examiner* — Mark S Rushing
(74) *Attorney, Agent, or Firm* — Barnes & Thornburg LLP

(57) ABSTRACT

An incontinence detection system includes an incontinence detection pad underneath a patient's pelvic area for detecting an incontinence event. The incontinence detection system further includes a moisture detection sensor, a gas detection sensor, and a reader. The moisture detection sensor is embedded in the incontinence detection pad for detecting a presence of moisture in incontinence detection pad. The gas detection sensor is positioned near the incontinence detection pad for detecting a presence of targeted gas, such as methane. The reader is communicatively coupled to the moisture detection sensor and the gas detection sensor to receive moisture data and gas data, respectively. The reader is configured to determine a type of the incontinence event based on the received moisture data and the gas data and transmit a signal indicative of the type of incontinence event to a server.

25 Claims, 6 Drawing Sheets

(51) Int. Cl.
*A61B 90/98* (2016.01)
*A61G 12/00* (2006.01)
*A61B 5/00* (2006.01)
*A61B 5/20* (2006.01)
*A61B 10/00* (2006.01)
*A61F 5/48* (2006.01)
*G16H 10/60* (2018.01)
*G16H 40/67* (2018.01)
*A61F 13/84* (2006.01)
*A61F 13/15* (2006.01)
*G16H 80/00* (2018.01)

(52) U.S. Cl.
CPC . *A61B 2010/0083* (2013.01); *A61B 2562/029* (2013.01); *A61F 2013/15056* (2013.01); *A61F 2013/15154* (2013.01); *A61F 2013/424* (2013.01); *A61F 2013/8473* (2013.01); *A61F 2013/8482* (2013.01); *G16H 10/60* (2018.01); *G16H 40/67* (2018.01); *G16H 80/00* (2018.01)

(58) Field of Classification Search
CPC ............ A61F 2013/8473; A61G 12/00; G16H 80/00; G16H 10/60; G16H 40/67
USPC ....................................................... 340/573.5
See application file for complete search history.

(56) References Cited

U.S. PATENT DOCUMENTS

| | | | |
|---|---|---|---|
| 7,642,396 B2 | 1/2010 | Ales, III et al. | |
| 8,698,641 B2 | 4/2014 | Abraham et al. | |
| 8,933,292 B2 | 1/2015 | Abraham et al. | |
| 9,107,776 B2 | 8/2015 | Bergman et al. | |
| 9,119,748 B2 | 9/2015 | Abraham et al. | |
| 9,545,342 B2 | 1/2017 | Cretu-Petra | |
| 9,927,410 B2 | 3/2018 | Carney et al. | |
| 2004/0220538 A1* | 11/2004 | Panopoulos | A61F 13/42 604/361 |
| 2007/0142799 A1 | 6/2007 | Ales et al. | |
| 2007/0252713 A1* | 11/2007 | Rondoni | A61B 5/202 340/573.5 |
| 2008/0228157 A1* | 9/2008 | McKiernan | A61F 13/42 604/361 |
| 2010/0150348 A1* | 6/2010 | Fairbanks | H04L 9/3226 380/255 |
| 2011/0092890 A1* | 4/2011 | Stryker | A61F 7/007 604/23 |
| 2011/0095884 A1 | 4/2011 | Xu et al. | |
| 2012/0119915 A1 | 5/2012 | Clement et al. | |
| 2012/0206265 A1 | 8/2012 | Solazzo et al. | |
| 2012/0268278 A1 | 10/2012 | Lewis et al. | |
| 2012/0310192 A1 | 12/2012 | Suzuki et al. | |
| 2013/0110064 A1* | 5/2013 | Richardson | A61F 13/42 604/361 |
| 2013/0267791 A1* | 10/2013 | Halperin | A61B 5/6892 600/300 |
| 2014/0276504 A1 | 9/2014 | Heil et al. | |
| 2015/0022343 A1* | 1/2015 | Sanders | A61B 5/4806 340/521 |
| 2015/0301004 A1* | 10/2015 | Carney | G01N 33/0047 73/31.01 |
| 2015/0330958 A1* | 11/2015 | Carney | A61F 13/42 73/23.34 |
| 2016/0374626 A1 | 12/2016 | Heil et al. | |
| 2017/0065464 A1 | 3/2017 | Heil et al. | |
| 2017/0246063 A1 | 8/2017 | Monson et al. | |
| 2018/0021184 A1 | 1/2018 | Monson et al. | |
| 2018/0253957 A1* | 9/2018 | Jhangiani | A61F 13/42 |

* cited by examiner

INCONTINENCE DETECTION SYSTEM CAPABLE OF IDENTIFYING URINARY OR FECAL INCONTINENCE The present application claims the benefit, under 35 U.S.C. § 119(e), of U.S. Provisional Application No. 62/491,466, filed Apr. 28, 2017, which is hereby incorporated by reference herein in its entirety.

BACKGROUND

The present disclosure relates to incontinence pads that sense patient incontinence. More specifically, the present disclosure relates to disposable incontinence pads of hospital beds, medical beds, or other types of beds in which the disposable incontinence pads are designed to absorb liquid in case of incontinent events.

In a care facility, such as a hospital or a nursing home, patients are often placed on patient support apparatuses for an extended period of time. Some patients who are positioned on the patient support apparatuses may have a risk of developing certain skin conditions, such as bed sores (also known as pressure sores or decubitus ulcers), due to heat and moisture present at the interface of the patient and the surface of a bed mattress. In an effort to mitigate or prevent such conditions, various devices have been proposed for detecting the presence of moisture, i.e., the presence of urinary incontinence and/or fecal incontinence. While various incontinence pads have been developed, in certain applications there is still room for improvement. Thus, a need persists for further contributions in this area of technology.

SUMMARY

The present application discloses one or more of the features recited in the appended claims and/or the following features which, alone or in any combination, may comprise patentable subject matter:

According to the present disclosure, an incontinence detection system may include an incontinence detection pad that may have a moisture detection sensor, a gas detection sensor that may be positioned near the incontinence detection pad, and a reader. The moisture detection sensor may be configured to detect a presence of moisture in the incontinence detection pad and the gas detection sensor may be configured to detect a presence of targeted gas. The reader may be communicatively coupled to the moisture detection sensor and the gas detection sensor to receive moisture data and gas data, respectively. The reader may be further configured to determine a type of incontinence based on the moisture data and gas data and may transmit a signal indicative of the type of incontinence event to a server.

In some embodiments, the type of incontinence event may include a urinary incontinence and a fecal incontinence. The moisture data produced by the moisture detection sensor may indicate whether moisture is detected in the incontinence detection pad. The gas data produced by the gas detection sensor may indicate whether the targeted gas is detected in surrounding air near the incontinence detection pad. The targeted gas may be methane, for example.

In some embodiments, the reader may be further configured to determine a level of the targeted gas that may be present in surrounding air. The reader may be further configured to determine whether the level of the targeted gas exceeds a predefined threshold and may issue an alert notification in response to a determination that the level of the targeted gas is greater than the predefined threshold. The predefined threshold may be based on a level of the targeted gas normally found in the atmosphere.

In some embodiments, the moisture detection sensor may be a Radio Frequency Identification (RFID) tag and a plurality of electrodes may be coupled to the RFID tag. The moisture detection sensor may be configured to communicate with the reader that may evaluate the transmitted signal to determine the status of the incontinence detection pad.

In some embodiments, the reader may be an RFID reader. The reader may be further configured to wirelessly communicate with the server to alert a caregiver of the status of the incontinence detection pad. The server may be included in a nurse call system and/or the server may be included in an electronic medical record (EMR) system. The server may be configured to communicate with a mobile device or a smart device of a caregiver.

In some embodiments, the reader may be further configured to communicate with the server to alert a caregiver of the status of the incontinence detection pad via a wired connection. The wired connection may include a nurse call cable, for example.

In a second aspect of the present disclosure, an incontinence detection system may include an incontinence detection pad, a first moisture detection sensor, a second moisture detection, and a reader. The first moisture detection sensor may be coupled to the incontinence detection pad and may be configured to detect a presence of moisture in the incontinence detection pad. The second moisture detection sensor may be coupled to the first moisture detection sensor via a tunnel that may be defined within a fluid impermeable material. The tunnel may contain a moisture wicking material. The reader may be communicatively coupled to the first and second moisture detection sensors to receive moisture data. The reader may be configured to transmit a signal that may be indicative of a type of incontinence event to a server.

In some embodiments, the first moisture detection sensor may be configured to transmit first moisture data to the reader and the second moisture detection sensor may be configured to transmit second moisture data to the reader. The first and second moisture data may be indicative of a presence or absence of moisture that may be detected at the corresponding sensor.

In some embodiments, the reader may be configured to determine a time between a time at which the first moisture sensor may have detected a presence of moisture and a time at which the second moisture sensor may have detected a presence of moisture. The reader may be configured to determine a travel time of detected moisture between the first moisture sensor and the second moisture sensor. The travel time may be a time difference between a time at which the first moisture sensor may have detected a presence of moisture and a time at which the second moisture sensor may have detected a presence of moisture. The moisture data may be timestamped when transmitted to the reader. The reader may be configured to (i) compare the travel time with a predefined threshold and (ii) determine a type of incontinence event based on the travel time between the first and second moisture detection sensors.

In a third aspect of the present disclosure, a method of detecting a type of an incontinence event may be provided. The method may include (i) receiving moisture data from a moisture detection sensor that may be contained in an incontinence detection pad, (ii) receiving gas data from a gas detection sensor that may be positioned near the incontinence detection pad, (iii) analyzing the moisture data to detect a presence of moisture in the incontinence detection pad, (iv) analyzing the gas data to detect a presence of targeted gas, (v) determining a type of incontinence based on the moisture data and gas data, and (vi) transmitting a signal indicative of the type of detected incontinence event to a server.

In some embodiments, the type of incontinence event may include a urinary incontinence and a fecal incontinence. The moisture data produced by the moisture detection sensor may indicate whether moisture is detected in the incontinence detection pad. The gas data produced by the gas detection sensor may indicate whether the targeted gas is detected in surrounding air near the incontinence detection pad. The targeted gas may be methane. However, the targeted gas may be any gas that may be present in human flatus or feces.

In some embodiments, the method may further include determining a level of the targeted gas that may be present in air surrounding the gas detection sensor, determining whether the level of the targeted gas is greater than a predefined threshold, and issuing an alert notification in response to a determination that the level of the targeted gas is greater than the predefined threshold. The predefined threshold may be based on a base level of the targeted gas that may be normally found in the atmosphere.

In some embodiments, the method may further include wirelessly communicating with the server to alert a caregiver of the status of the incontinence detection pad. The moisture detection sensor may be a Radio Frequency Identification (RFID) tag and a plurality of electrodes may be coupled to the RFID tag.

In some embodiments, the server may be included in a nurse call system and/or in an electronic medical record (EMR) system. The server may be configured to communicate with a mobile device or a smart device of a caregiver. The method may further include communicating with the server to alert a caregiver of the status of the incontinence detection pad via a wired connection. The wired connection may include a nurse call cable, for example.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
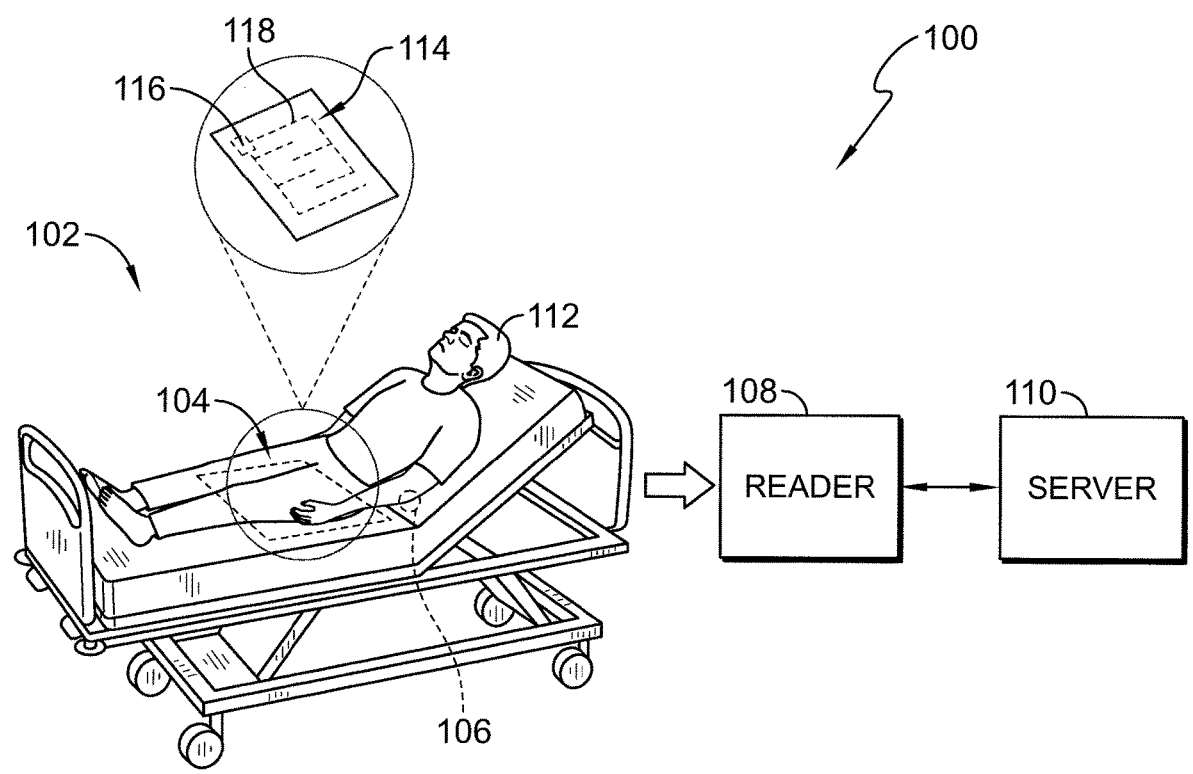
FIG. 1 is a schematic perspective view of a incontinence detection system including an incontinence detection pad positioned on a patient support apparatus and a gas detection sensor positioned on the patient support apparatus.

For the purposes of promoting an understanding of the principles of the invention, reference will now be made to one or more illustrative embodiments shown in the drawings and specific language will be used to describe the same. It will nevertheless be understood that no limitation of the scope of the invention is thereby intended.

Referring now to FIG. 1, an illustrative incontinence detection system 100 is configured to detect an incontinence event of a patient and determine a type of incontinence (e.g., urinary incontinence or fecal incontinence). It should be appreciated that by determining the type of incontinence, a caregiver can determine whether the patient requires immediate attention. For example, the caregiver may attend to a patient with a higher priority fecal incontinence. The illustrative incontinence detection system 100 is used with a patient support apparatus 102 and includes an incontinence detection pad 104, a gas detection sensor 106, a reader 108, and, optionally, a server 110. The illustrative patient support apparatus 102 is embodied as a hospital bed. It should be appreciated that in some embodiments, the patient support apparatus 102 may be embodied as a residential bed, a chair, a wheelchair, a mattress, a stretcher, a patient transport device, or any other type of person support apparatus.

The illustrative incontinence detection pad 104 is configured to wick or absorb any excreta discharged from a patient's body, such as sweat, urine, or feces, to draw the moisture away from a patient 112. To do so, the incontinence detection pad 104 is adapted to underlie the patient 112 lying on the patient support apparatus 102. Specifically, the incontinence detection pad 104 is positioned atop the patient support apparatus 102 and configured to underlie a pelvic region of the patient 112 supported on the patient support apparatus 102. The pelvic region is most susceptible to moisture buildup from incontinence events. In other embodiments, the incontinence detection pad 104 may be integrated into the patient support apparatus 102, such as being integrated into a mattress. In still other embodiments, the incontinence detection pad 104 may be integrated within an undergarment or other article of clothing or the incontinence detection pad 104, itself, is a diaper or disposable undergarment.

The incontinence detection pad 104 further includes a moisture detection sensor 114 for detecting presence of moisture in the incontinence detection pad 104. The illustrative moisture detection sensor 114 includes a plurality of electrodes 118 and a moisture sensor tag 116. The plurality of electrodes 118 is connected to and extends from the moisture sensor tag 116, which is discussed in detail below. In the illustrative embodiment, the moisture sensor tag 116 is embodied as an RFID (Radio Frequency Identification) tag 116. It should be appreciated that in some embodiments, the moisture detection sensor 114 may be any sensor that is capable of detecting moisture presence. The RFID tag 116 used in the incontinence pad 104 is a passive tag or chip that communicates with an associated reader 108 by using the electromagnetic field generated by one or more antennae coupled to the reader 108 to power the RFID tag 116. In some embodiments, a semi-passive or active RFID tag 116 may be used. The RFID tag 116 is configured to communicate with RFID reader 108 to send moisture data, and the reader 108 or other processing circuitry determines whether the incontinence detection pad 104 is wet or dry by evaluating the moisture data received from the RFID tag 116. The reader 108 is further configured to periodically communicate with the server 110 of the incontinence detection system 100 to transmit the moisture data indicative of a moisture status of the incontinence detection pad 104. In some embodiments, the moisture sensor 118 may only transmit the moisture data to the reader 108 when detecting moisture presence in the incontinence detection pad 104.

In addition, the incontinence detection system 100 further includes the gas detection sensor 106 that communicates with the reader 108. In the illustrative embodiment, as shown in FIG. 1, the gas detection sensor 106 is position on the patient support apparatus 102 close to the patient's pelvic area. It should be appreciated that the gas detector sensor 106 may be positioned at any suitable location on the patient support apparatus 102. For example, in some embodiments, the gas detector sensor 106 may be attached to a frame of the patient support apparatus 102 that supports the mattress. In other embodiments, the gas detector sensor 106 may be attached to one or more siderails of the patient support apparatus 102.

The gas detection sensor 106 is configured to detect a presence of targeted gas in human flatus and/or feces, such as methane, in the surrounding air. For example, in some embodiments, the gas detection sensor 106 may be an air quality sensor. In the illustrative embodiment, the gas detection sensor 106 is configured to periodically communicate with the reader 108 to transmit gas data indicative of presence or absence of the targeted gas. The reader 108 or other processing circuitry determines whether the targeted gas is detected in air surrounding the gas detection sensor 106 by evaluating the received gas data. It should be appreciated that, in some embodiments, incontinence detection system 100 may include a second reader (not shown) for the gas detection sensor 106. In such embodiments, the gas detection sensor 106 may communicate with the second reader to transmit the gas data to be evaluated by the second reader. In some embodiments, the gas detection sensor 106 may determine whether the targeted gas is present and only transmit the gas data to the reader 108 when detecting targeted gas presence.

Additionally, in the illustrative embodiment, the reader 108 determines a level of the targeted gas present in air surrounding the gas detection sensor 106 based on the received gas data and determines whether the determined level of the targeted gas is greater than a predefined level or threshold. It should be appreciated that the predefined threshold is based on a base level of the targeted gas normally found in the atmosphere. It should be appreciated that the predefined level may be manually adjusted based on the level of the targeted gas detected in air surrounding the gas detected 106 and/or the level of the targeted gas detected in flatus of the patient 112 supported on the patient support apparatus 102. The illustrative gas detection sensor 106 may periodically transmit the gas data and/or the level of the targeted gas to the server 110. In some embodiments, the gas detection sensor 106 may transmit the gas data and/or the level of the targeted gas to the server 110 when the level of the targeted gas exceeds the predefined threshold.

In the illustrative embodiment, the server 110 is configured to receive a detection of an incontinence event and a type of incontinence from the reader 108. For example, the server 110 may be embodied as a server included in a nurse call system and/or an EMR (electronic medical record) system or even a server configured to communicate with a caregiver's mobile or smart device. In some embodiments, the reader 108 may communicate via Wi-Fi or other known wireless communication equipment and protocols. Alternatively or additionally, the reader 108 may communicate the incontinence event via a wired connection, such as a nurse call cable. In some embodiments, the incontinence detection system 100 may further include a local alert (not shown) on bed 102 or nearby bed 102 for alerting detected incontinence events. In the illustrative embodiment, the reader 108 is configured to determine a type of incontinence based on the moisture data and the gas data received from the moisture sensor 114 and the gas detection sensor 106, respectively, which is described in detail below. It should be appreciated that, in some embodiments, the reader 108 may transmit the moisture data and gas data to the server 110 to be evaluated. In such embodiments, the server 110 may evaluated the received moisture and gas data to determine the presence of moisture and/or targeted gas.

Figure 2:
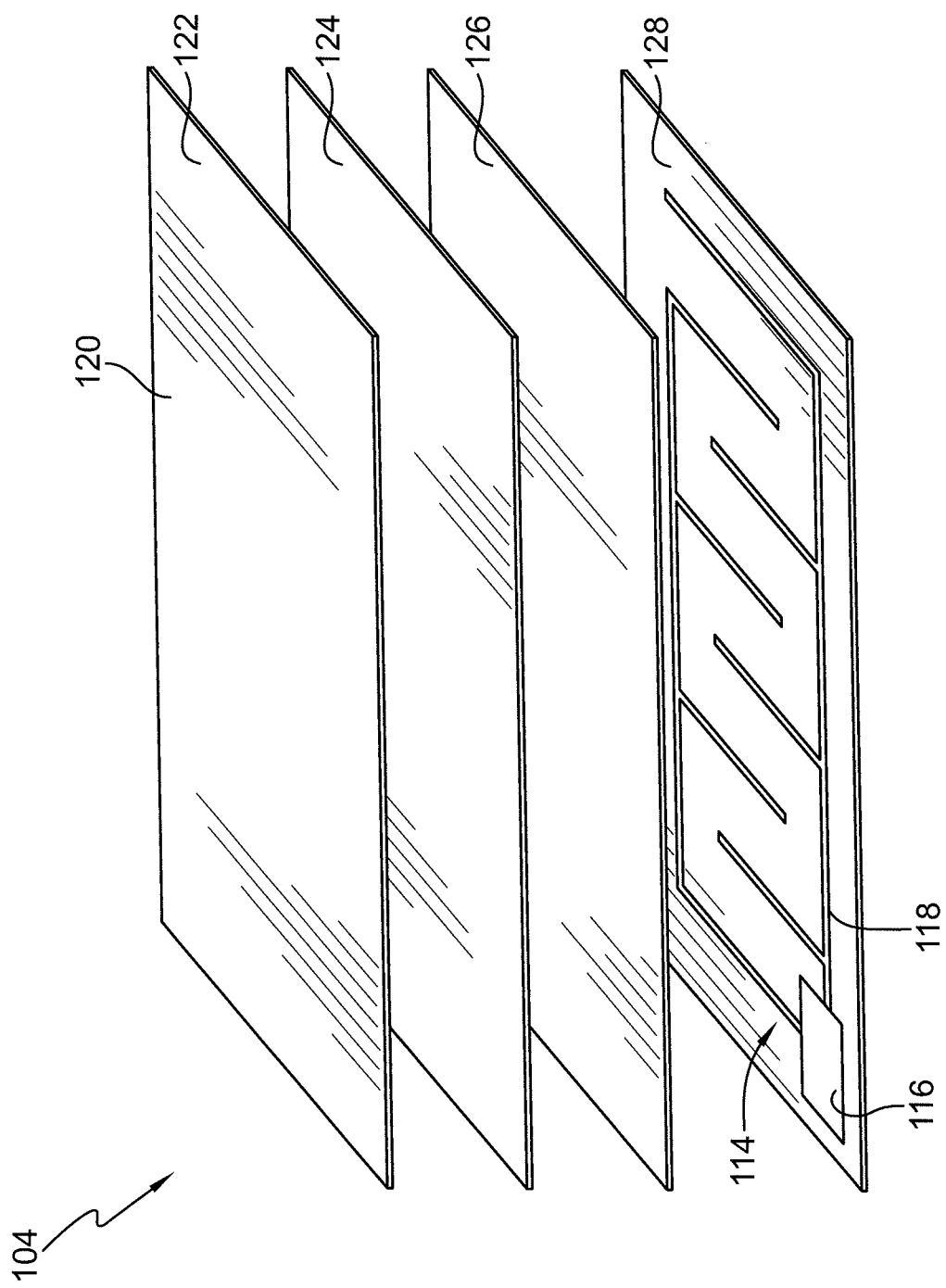
FIG. 2 is an exploded perspective view of a first embodiment of an incontinence detection pad for detecting moisture presence indicative of an incontinence event and determining a type of incontinence.

Referring to FIG. 2, an illustrative embodiment showing how the moisture detection sensor 114 for detecting moisture can be incorporated into an incontinence detection pad 104. The incontinence detection pad 104 includes a top layer 122 including a non-woven material, an optional acquisition distribution layer 124, an absorbent layer 126, a barrier layer 128, and the moisture detection sensor 114 implemented as a part of the barrier layer 128.

The non-woven top layer 122 is typically a polymer-based material and is made from bonded fibers and/or filaments. The non-woven top layer 122 provides comfort and softness for a patient on the incontinence detection pad 104.

The optional acquisition distribution layer 124 includes a moisture-wicking material that is horizontally oriented within the acquisition distribution layer 124. For example, in the illustrative embodiment, the moisture-wicking material is nonwoven and non-linear polymeric or pulp fibers that are horizontally oriented into a nonwoven web structure. The orientation of the moisture-wicking material of the acquisition distribution layer 124 is adapted to provide capillary action or wicking properties to direct moisture in a horizontal direction to draw the moisture toward peripheral regions of the acquisition distribution layer 124. In some embodiments, the moisture-wicking material may form a density gradient across the acquisition distribution layer 124 such that a density of the moisture-wicking material increases from a center to the peripheral regions of the acquisition distribution layer 124. In such embodiments, the density gradient of the moisture-wicking material provides a further capillary action to direct moisture in the horizontal direction to draw the moisture from the center toward the peripheral regions of the acquisition distribution layer 124. The remaining moisture or liquid in the acquisition distribution layer 124 travels downwardly (e.g., by the force of gravity) into the absorbent layer 126. An exemplary incontinence detection pad that may be used in incontinence detection system 100 is shown and described in U.S. Patent Application No. 62/456,903, which was filed Feb. 9, 2017 and which is expressly incorporated herein by reference.

It should be appreciated that in some embodiments, the optional acquisition distribution layer 124 includes a moisture-wicking material that is vertically oriented within the acquisition distribution layer 124 to draw the moisture toward the absorbent layer 126. In yet other embodiments, the acquisition distribution layer 124 may be divided into two layers: a first layer (not shown) and a second layer (not shown) positioned underneath the first layer. In such embodiments, the first layer may include a moisture-wicking material that is vertically oriented within the first layer, and the second layer may include a moisture-wicking material that is horizontally oriented within the second layer. The first layer is adapted to provide capillary action or wicking properties to direct moisture in a vertical direction toward the second layer. Whereas, the second layer is adapted to provide capillary action or wicking properties to direct moisture in a horizontal direction to draw the moisture toward peripheral regions of the acquisition distribution layer 124. In some embodiments, the second layer may be positioned on top of the first layer. The remaining moisture or liquid in the acquisition distribution layer 124 travels downwardly (e.g., by the force of gravity) into the absorbent layer 126.

The absorbent layer 126 includes an absorbent material, such as a three-dimensional fibrous or woven material. For example, the absorbent layer 126 may be made of a super absorbent polymer (SAP) material which provides 3-5 times more moisture absorption than the materials of the acquisition distribution layers 124 described above. In some embodiments, an increasing density gradient is also formed downwardly or vertically from an upper surface to a bottom surface of the absorbent layer 126. Such vertical arrangement of the absorbent material provides capillary action or wicking properties to direct moisture in a vertical direction. The absorbent layer 126 is configured to absorb the moisture and draw the moisture downwardly toward the moisture detection sensor 114 of the barrier layer 128.

The barrier layer 128 is made of a fluid impermeable material which provides a barrier to prevent moisture penetration to a mattress support surface or frame beneath the incontinence detection pad 104. For example, in the illustrative embodiment, the impermeable material is a polyethylene (PE) sheet. In other embodiments, the impermeable material may be polypropylene (PP) sheets and/or polyurethane (PU) sheets. The barrier layer 128 may or may not be breathable. In some embodiments, the barrier layer 128 is substantially waterproof. As discussed above, the barrier layer 128 further includes a moisture detection sensor 114 for detecting moisture presence and, in some embodiments, moisture volume.

As described above, the moisture detection sensor 114 includes the RFID tag 116 and the plurality of electrodes 118 connected to and extending from the RFID tag 116. In the illustrative embodiment, the plurality of electrodes 118 is printed on the barrier layer 128. The electrodes 118 are made of a conductive material, such as carbon, silver, copper, zinc and graphene.

In case of an incontinence event, the patient's excreta travels downwardly (e.g., by the force of gravity) past the top layer 122 into the acquisition distribution layer 124. The acquisition distribution layer 124 is configured to provide the moisture wicking in the direction towards the peripheral region of the incontinence detection pad 104. The remaining moisture or liquid in the acquisition distribution layer 124 travels downwardly (e.g., by the force of gravity) into the absorbent layer 126. As discussed above, the absorbent layer 126 is configured to absorb the moisture and draw the moisture downwardly toward a bottom of the absorbent layer 126 towards the moisture detection sensor 114 of the barrier layer 128.

Figure 3:
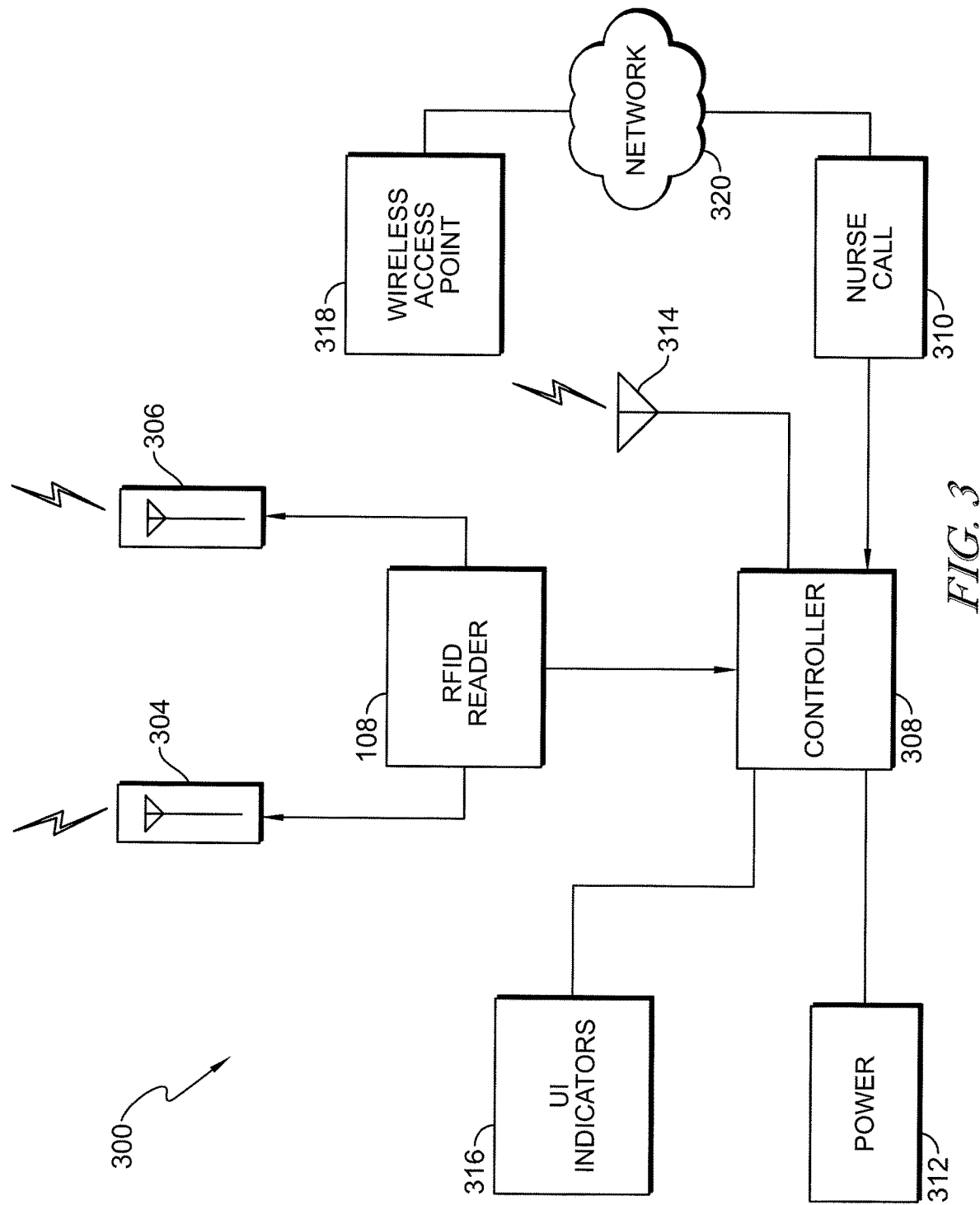
FIG. 3 is a block diagram of a communication system formed by components of the incontinence detection system of FIG. 1 and components of a network of a healthcare facility.

Referring now to FIG. 3, a communications system 300 is configured to communicate with the moisture detection sensor 114 and the gas detection sensor 106 of the incontinence detection system 100. An RFID reader 108 employs a pair of antennas 304, 306 that are signaled by the RFID reader 108 to periodically poll the moisture detection sensor 114 and the gas detection sensor 106 to report a moisture event and/or a gas event has occurred. In other embodiments, gas sensor 106 coupled to the reader 108 via a wired connection for communication therewith. Energy from antennas 304, 306 is used by the passive RFID tag 116 to power it to return incontinence detection information back to either or both of antennas 304, 306. The detected event is relayed to a controller 308 which is configured with software to communicate the incontinence detection information to an appropriate caregiver or system. In the illustrative embodiment, the controller 308 is also coupled to user interface (UI) indicators 316, such as lights or a graphical display on a patient bed or on a room wall or other piece of nearby equipment, to indicate locally whether the incontinence detection pad 104 is wet or dry. Additionally, the controller 308 is also connected to a power source 312 and a wireless communications device, such as a Wi-Fi antenna 314, in order to communicate the sensed incontinence event with other associated systems such as a nurse call system 310 via a wireless access point 318 and network 320. It should be appreciated that the nurse call system 310 is communicatively coupled to the controller 308.

In the illustrative embodiment, the sensor system or incontinence detection pad 104 and communication system 300 are implemented as part of a remote alert system. As described above, the incontinence detection pad 104 is placed between a patient and an underlying mattress of a patient bed 102 beneath the patient's pelvic area. In some embodiments, the incontinence detection pad 104 is integrated into a mattress to form a part thereof, but is removable for replacement with a clean incontinence detection pad 104 after an incontinence event occurs. The antennas 304, 306 of communications system 300 are mounted to a frame of bed 102, such as being mounted to an upper surface of a mattress support deck.

In the illustrative embodiment, the controller 308 is coupled to the frame of the bed 102. In some embodiments, the controller 308 may be positioned in a housing that also contains the RFID reader 108. In other embodiments, separate housings are used to contain these elements. It should be appreciated that the antennas 304, 306 are in communication with the reader 108 and with the controller 308. Upon detection of a moisture event, the controller 308 communicates with circuitry of bed 102 to activate one or more in-room alerts such as indicators or illuminating devices (not shown) that are located on bed 102 and that are easily viewed by a caregiver. Additionally or alternatively, the controller 308 may communicate the event to devices for remote alerting such as a status board or other visual display of a hospital information system, a hallway call light such as a light in a dome light or alert light assembly, a computer monitor of a nurse call system and/or an electronic medical records (EMR) system, or even a caregiver's mobile device.

The controller 308 communicates the moisture event via Wi-Fi antenna 314 or other known wireless communication equipment and protocols in some embodiments. Alternatively or additionally, the controller 308 communicates the moisture event via a wired connection, such as a 37-pin nurse call cable. It will be appreciated that a healthcare facilities' network infrastructure serves as an intermediary between system 300 and the one or more remote alerting devices with which system 300 communicates. Thus, wireless access points, gateways, routers, cabling, connection ports, jacks, and the like are the type of equipment.

In some embodiments, information indicating that the pad is dry or that no moisture event has occurred is communicated by controller 308 to one or more remote computer devices, such as an EMR computer, for storage in a patient's EMR. Such information is communicated at pre-set intervals, such as every hour or every half hour or more or less frequently, for example. The interval for communicating such information is programmable by caregivers in some embodiments. Further alternatively or additionally, a caregiver selects a user input such as an icon on a graphical display of a patient bed or at remote computer to command the reader to poll the incontinence pad to obtain information regarding the wet/dry status of the pad. By permitting the caregiver to determine when the incontinence pad status information is received, alert fatigue is avoided because the caregiver receives the information when the caregiver is able to act on it.

Figure 4:
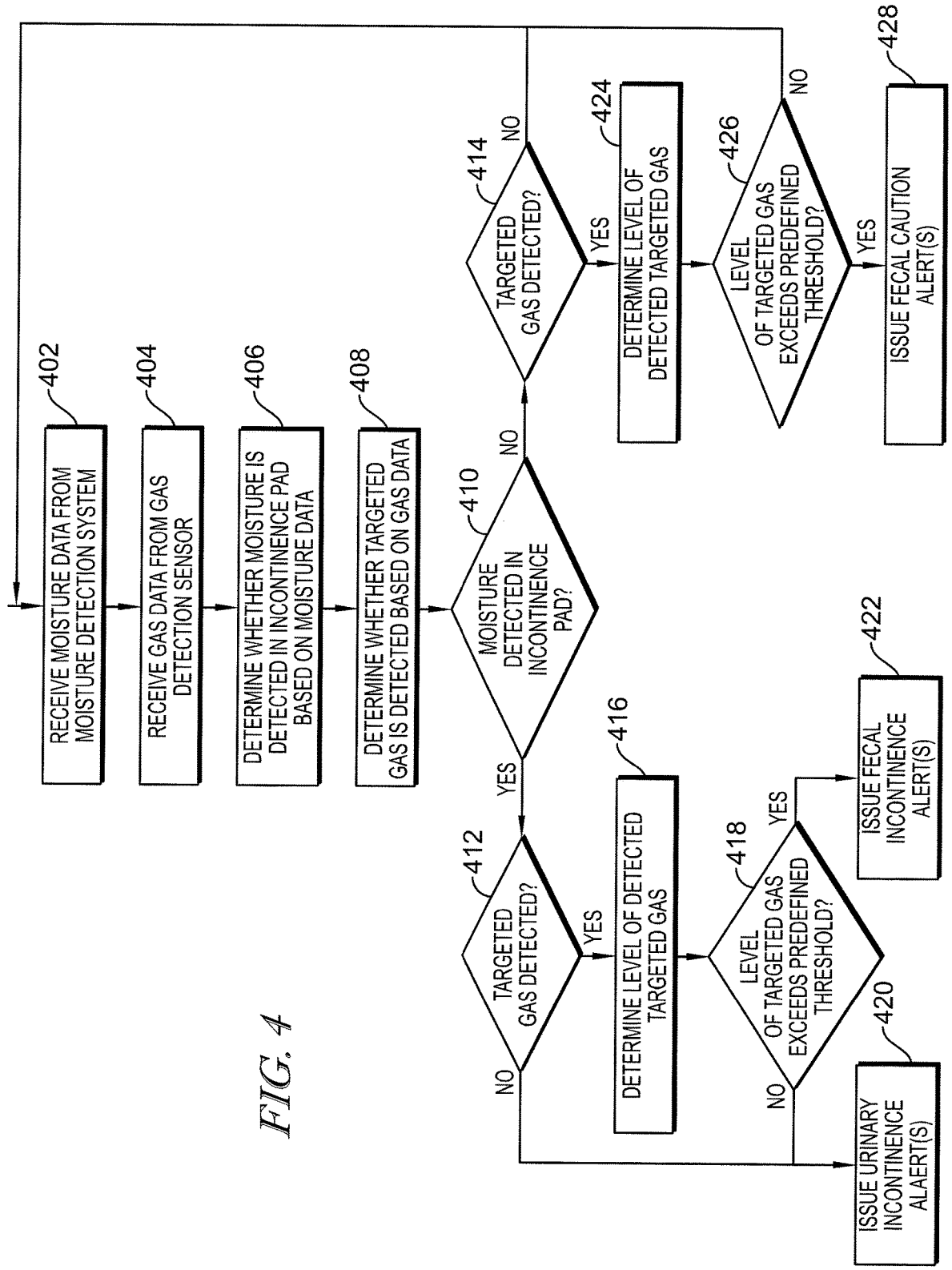
FIG. 4 is a flow diagram of at least one embodiment of a method for determining a type of an incontinence event using the incontinence detection pad and gas detection sensor of FIGS. 1-3.

Referring now to FIG. 4, in use, the reader 108 of the incontinence detection system 100 executes a method 400 for determining a type of an incontinence event. The method 400 begins at block 402 in which the reader 108 receives moisture data from the moisture detection sensor 114 indicating a moisture status of the incontinence detection pad 104. In block 404, the reader 108 receives gas data from the gas detection sensor 106 indicating presence or absence of targeted gas which is present in feces. In block 406, the reader 108 determines whether the moisture is detected in the incontinence detection pad 104 based on the received moisture data from the moisture detection sensor 114. In block 408, the reader 108 determines whether the targeted gas is detected in the incontinence detection pad 104 based on the received gas data from the gas detection sensor 106.

In block 410, if the reader 108 determines that the moisture is detected in the incontinence detection pad 104, the method 400 advances to block 412. If not, the method 400 advances to block 414.

In block 412, the reader 108 further determines whether the targeted gas is detected based on the gas data received from the gas detection sensor 106. If the reader 108 determines that the targeted gas is not detected, the method 400 skips ahead to block 420 in which the reader 108 issues a urinary incontinence alert(s). If, however, the reader 108 determines that the targeted gas is present, the method 400 advances to block 416 in which the reader 108 determines a level or amount of the detected targeted gas.

In block 418, the reader 108 further determines whether the determined level of the targeted gas exceeds a predefined threshold. For example, as described above, the predefined threshold may be a base level or base amount of the targeted gas normally found in the atmosphere. If the reader 108 determines that the level of targeted gas does not exceed the predefined threshold, the method 400 advances to block 420 in which the reader 108 issues a urinary incontinence alert(s). If, however, the reader 108 determines that the level of targeted gas exceeds the predefined threshold, the method 400 advances to block 422 in which the reader issues a fecal incontinence alert(s).

When the moisture is not detected in the incontinence pad 104, in block 414, the reader 108 further determines whether the targeted gas is detected in block 408 based on the gas data received from the gas detection sensor 106. If the targeted gas is not present, the method 400 loops back to block 402 to continue receiving and monitoring the moisture data and gas data from the moisture detection sensor 114 and gas detection sensor 106, respectively. If, however, the targeted gas is detected, the method advances to block 424 in which the reader 108 further determines the level of the detected targeted gas.

In block 426, the reader 108 determines whether the determined level of the detected targeted gas exceeds a predefined threshold. If the reader 108 determines that the level of the targeted gas does not exceed the predefined threshold, the method 400 loops back to block 402 to continue receiving and monitoring the moisture data and gas data from the moisture detection sensor 114 and gas detection sensor 106, respectively. If, however, the reader 108 determines that the level of the targeted gas exceeds the predefined threshold, the method 400 advances to block 428 in which the reader 108 issues a fecal caution alert(s), which indicates that the patient 112 has potentially expelled feces. For example, the fecal caution alert is configured to alert the caregiver of flatus activity of the patient 112, which may infer a likelihood of a defecation event currently or potentially in the near future.

While the method 400 has been described above as being carried out by reader 108, it is within the scope of this disclosure for some or all of the steps of method 400 to be carried out by server 110, controller 308, nurse call computer 310 or some other computer of network 320.

Referring now to FIGS. 5-9, another embodiment of an incontinence detection system 500 is shown. The embodiment of FIG. 5 includes many of the same features described above in regard to FIGS. 1 and 2. The same reference numbers are used in FIG. 5 to identify features that are the same or similar to those described above in regard to FIGS. 1 and 2. The illustrative incontinence detection system 500 illustrates how an incontinence detection pad 502 for detecting an incontinence event can further determine a type of the incontinence event. To do so, the incontinence detection system 500 includes the incontinence detection pad 502, a reader 108, and a server 110. It should be appreciated that the characteristics of the layers of the incontinence detection pad 502 is similar to the moisture detection pad 104.

Figure 5:
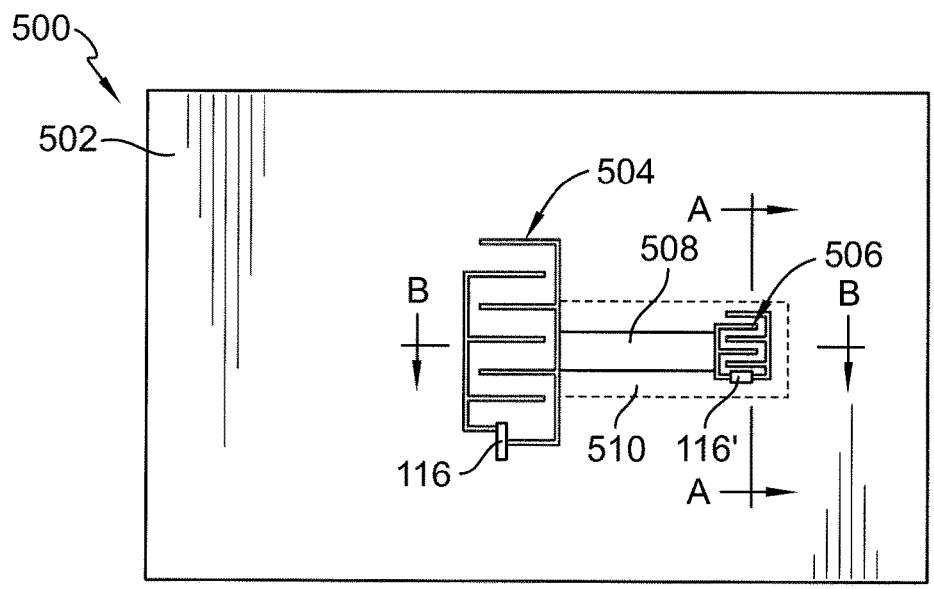
FIG. 5 is a top plan view of a portion of a second embodiment of an incontinence detection pad having first and second sensors for detecting moisture presence indicative of an incontinence event and determining a type of incontinence.

As shown in FIG. 5, the incontinence detection pad 502 includes a first moisture detection sensor 504, a second detection sensor 506 connected to the first moisture detection sensor 504 via a moisture-wicking material 508, and a fluid impermeable material 510 that is configured to isolate or protect the second detection sensor 506 and the moisture-wicking material 508. In the illustrative embodiment, the first and second moisture detection sensors 504, 506 are coupled to barrier layer 128 and the first moisture detection sensor 504 is generally positioned at the center of the incontinence detection pad 502. It should be appreciated that a pelvic region of a patient is generally positioned at the center of the incontinence detection pad as well.

The moisture-wicking material 508 is configured to draw the moisture from the first moisture detection sensor 504 to the second moisture detection sensor 506, which is positioned at the peripheral side of the moisture detection pad 104. In the illustrative embodiment, the moisture-wicking material 508 covers the second detection sensor 506 to allow the second detection sensor 506 to detect moisture from the moisture-wicking material 508. It should be appreciated that the fluid impermeable material 510 is configured to create a barrier between the moisture-wicking material 508 and the absorbent layer 126 to prevent the moisture-wicking material 508 from being in direct contact with the moisture present in the absorbent layer 126 of the incontinence detection pad 502. In other words, the fluid impermeable material 510 ensures that the detection of moisture by the second moisture detection sensor 506 is limited to the detection of moisture wicked from the first moisture detection sensor 504, which is discussed in more detail below.

Figure 6:
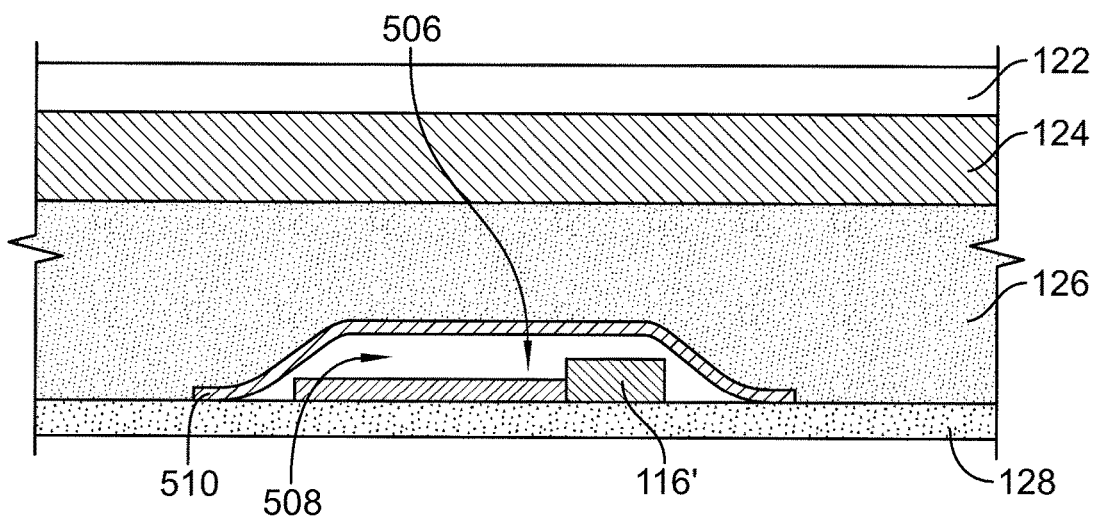
FIG. 6 is a cross sectional view taken along line A-A of FIG. 5 showing a first alternative construction of a fluid impermeable material of the incontinence detection pad isolating the second sensor from the overlying layers of the incontinence detection pad.
Figure 7:
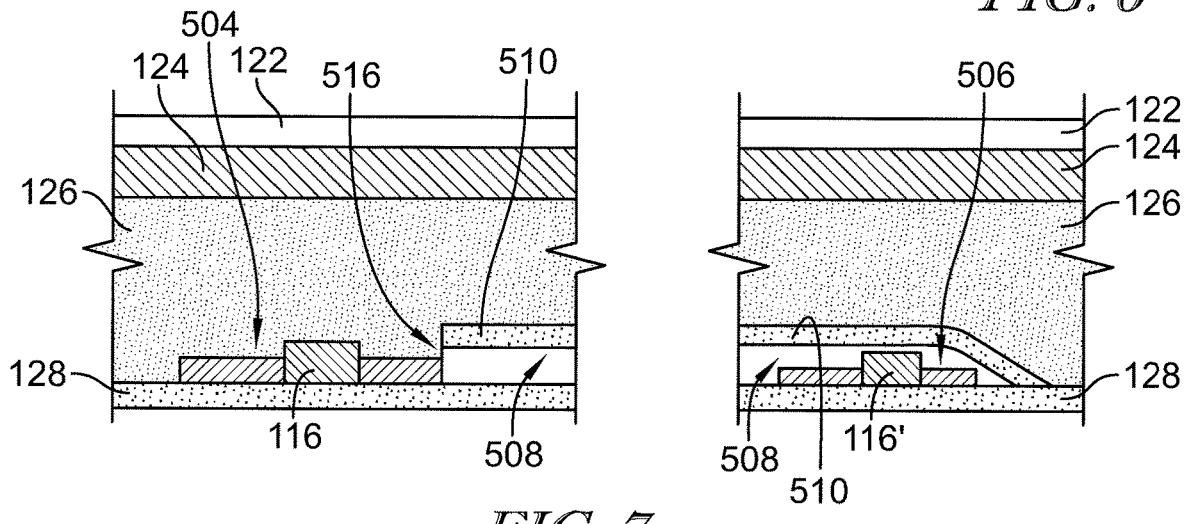
FIG. 7 is a cross sectional view taken along line B-B of FIG. 5 showing the first alternative construction of the fluid impermeable material of the incontinence detection pad forming a tunnel having an opening adjacent the first sensor and extending to the second sensor.

In some embodiments, as shown in FIGS. 6-7, the fluid impermeable material 510 may be embodied as a thin film-like material 510 that is attached to the barrier layer 128 to create a tunnel between the thin film-like material 510 and the barrier layer 128 in which the moisture-wicking material 508 and the second detection sensor 506 reside. As shown in FIG. 7, the moisture wicking material 508 is exposed to the absorbent layer 126 and the first sensor 504 at an opening 516 adjacent to the first moisture detection sensor 504. It should be appreciated that the moisture-wicking material 508 is horizontally orientated within the tunnel. The moisture wicking material 508 is configured to wick moisture that is present at the opening 516 near the first moisture detection sensor 504, which is likely to be detected by the first moisture detection sensor 504, toward the second moisture detection sensor 506. Thus, the moisture reaches the second moisture detection sensor 506 only through the tunnel after wicking through the moisture wicking material 508 over a period of time.

Figure 8:
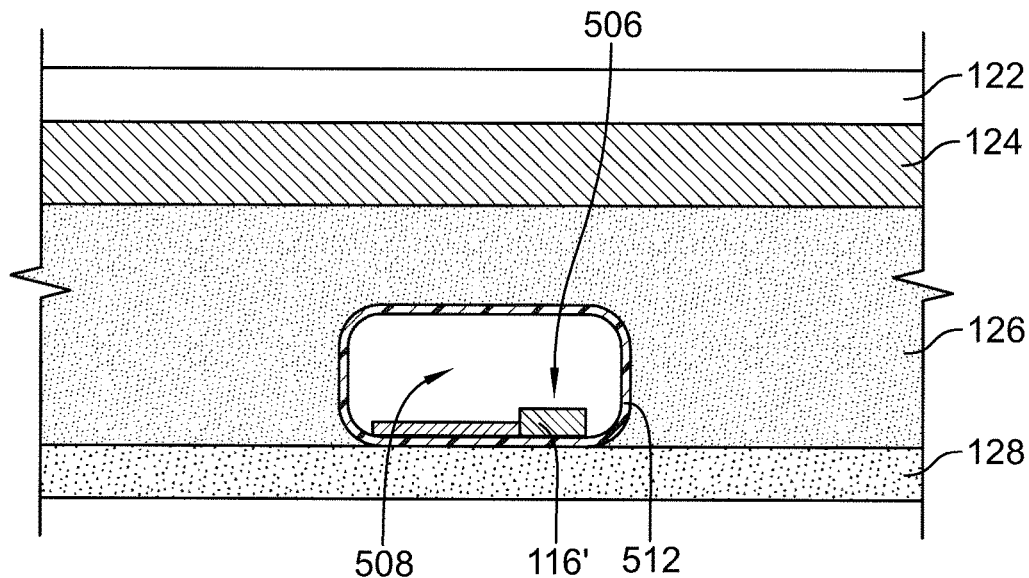
FIG. 8 is a cross sectional view taken along line A-A of FIG. 5 showing a second alternative construction of a fluid impermeable material of the incontinence detection pad forming a sheath within which the second sensor is situated and which isolates the second sensor from the overlying layers of the incontinence detection pad.
Figure 9:
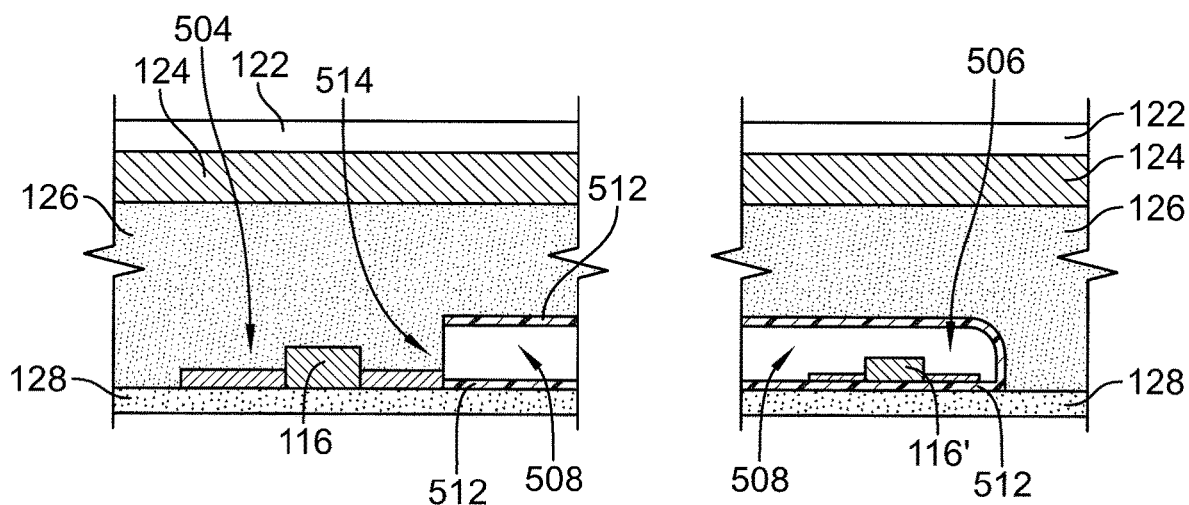
FIG. 9 is a cross sectional view taken along section line B-B of FIG. 5 showing the sheath of the second alternative construction of the fluid impermeable material of the incontinence detection pad forming a tunnel having an opening adjacent the first sensor and extending to the second sensor.

Alternatively, in other embodiments, as shown in FIGS. 8-9, the fluid impermeable material 510 may be embodied as a fluid impermeable sheath 512, such as plastic, that encases the moisture wicking material 508 and the second detection sensor 506. In such embodiments, the fluid impermeable sheath 512 serves as a tunnel through which moisture moves from region of the first moisture detection sensor 504 to the second moisture detection sensor 506. As shown in FIG. 9, the moisture wicking material 508 is exposed to the absorbent layer 126 at an opening 514 adjacent the first moisture detection sensor 504. It should be appreciated that the moisture-wicking material 508 is horizontally orientated within the tunnel. The moisture wicking material 508 is configured to wick moisture that is present at the opening 514 near the first moisture detection sensor 504, which is likely to be detected by the first moisture detection sensor 504, toward the second moisture detection sensor 506 over a period of time.

Referring back to FIG. 5, in the event of an incontinence event, the fluid travels downwardly toward the first moisture detection sensor 504 which is on the barrier layer 128. As discussed above, the barrier layer 128 is a liquid impermeable layer. As such, as the incontinence fluid further travels downwardly toward the first moisture detection sensor 504 through absorbent layer 126, the second moisture detection sensor 506 is not directly accessible from the absorbent layer 126. Instead, when the incontinence fluid reaches the first moisture detection sensor 504, the moisture contacts the moisture wicking material 508 exposed adjacent the first moisture detection sensor 504. The moisture wicking material 508 provides a capillary action to direct incontinence fluid in a horizontal direction to draw the incontinence fluid from the first moisture detection sensor 504 toward the second moisture detection sensor 506. As such, the moisture detection by the second moisture detection sensor 506 is limited to the detection of moisture drawn from the first moisture detection sensor 504.

When the incontinence fluid reaches the first moisture detection sensor 504, the moisture sensor tag 116 of the first moisture detection sensor 504 transmits first moisture data to the reader 108. It should be appreciated that the first moisture data may be timestamped. Subsequently, the fluid travels within the tunnel along the moisture wicking material 508 toward the second moisture sensor 504, where the second moisture sensor 504 subsequently detects the moisture. The moisture sensor tag 116' of the second moisture sensor 506 then transmits second moisture data to the reader 108. It should be appreciated that the second moisture data may also be timestamped. The reader 108 is configured to determine the time difference between the timestamp of the first moisture data and the timestamp of the second moisture data. In some embodiments, the reader 108 is configured to determine the time difference between the time at which the first moisture data is received by the reader 108 and the time at which the second moisture data is received by the reader 108.

Based on the time difference, the type of incontinence is determined. It should be appreciated that a different type of fluid has a different travel time along the moisture wicking material 508 due to different viscosity of the fluid. In other words, the travel time correlates with the viscosity of the fluid of detected incontinence event. For example, a fluid with higher viscosity will travel slower along the moisture wicking material 508 compared to a fluid with lower viscosity. As such, the fluid with higher viscosity will have a longer travel time from the first moisture detection sensor 504 to the second moisture detection sensor 506 than the fluid with lower viscosity. It should be appreciated that fecal incontinence has higher viscosity than urinary incontinence. Also, it should be noted that the fecal incontinence has moisture or fluid leeching out of it over a period of time such that the leeched moisture is what wicks through material 508 within the tunnel toward second moisture detection sensor 506 rather than the fecal matter, itself. However, this leeched moisture from the feces is considered to still be "feces" detected by sensor 206 according to this disclosure.

In some embodiments, the reader 108 may determine the travel time between which the first and second moisture detection sensors 504, 506 detect moisture and compare the travel time with a predefined threshold time. In such embodiments, the reader 108 determines whether the travel time is shorter or longer than the predefined threshold time. If the travel time is shorter than the threshold time, the reader 108 determines that the incontinence event is a urinary incontinence event. On the other hand, if the travel time is longer than the threshold time, the reader 108 determines that the incontinence event is a fecal incontinence event.

It should be appreciated that, in other embodiments, the reader 108 may compare the travel time with a urinary incontinence threshold time and a fecal incontinence threshold time. If the travel time is less than the urinary incontinence threshold time, the reader 108 issues alerts to a caregiver to check the incontinence detection pad 502. For example, the travel time may be less than the urinary incontinence threshold time when the amount of fluid present in the incontinence detection pad 502 is not enough. In some embodiments, the reader 108 may ignore such detection if the travel time is less than the urinary incontinence threshold time and continue to monitor the subsequent detection of an incontinence event.

If the travel time is between the urinary incontinence threshold time and the fecal incontinence threshold time, the reader 108 determines that the detected incontinence event is a urinary incontinence event. On the other hand, if the travel time is longer the fecal incontinence threshold time, the reader 108 determines that the detected incontinence event is a fecal incontinence event. Therefore, based on the time difference between the time at which the first moisture sensor 502 detected the presence of moisture and the time at which the second moisture sensor 504 detected the presence of moisture, the reader 108 can determine the type of incontinence and generate a corresponding alert notification.

The reader 108 is further configured to periodically communicate with the server 110 of the incontinence detection system 500 to transmit the moisture data indicative of the moisture status (i.e., the presence of incontinence event and the type of the incontinence event) of the incontinence detection pad 104. In some embodiments, the reader 108 may only transmit the moisture data to the server 110 when moisture is detected in the incontinence detection pad 104.

While the analysis of the travel time is described above as being carried out by reader 108, it is within the scope of this disclosure for some or all of the travel time analysis to be carried out by server 110, controller 308, nurse call computer 310 or some other computer of network 320.

Although certain illustrative embodiments and graphical illustrations have been described in detail above, variations and modifications exist within the scope and spirit of this disclosure as described and as defined in the following claims.

The invention claimed is:

1. An incontinence detection system for use with a patient bed having a frame and a mattress supported by the frame, the incontinence detection system comprising:
   an incontinence detection pad having a moisture detection sensor, the moisture detection sensor being configured to detect a presence of moisture in the incontinence detection pad;
   a gas detection sensor configured to detect a presence of targeted gas, the gas detection sensor being spaced from the incontinence detection pad and coupled to the frame of the patient bed underneath a central region of the mattress; and
   a reader communicatively coupled to the moisture detection sensor and the gas detection sensor to receive moisture data and gas data, respectively, the reader configured to determine a type of incontinence based on the moisture data and gas data and transmit a signal indicative of the type of incontinence event to a server, wherein the reader is configured to determine whether the gas data indicates that a level of the targeted gas is greater than a predefined threshold which is manually adjustable.

2. The incontinence detection system of claim 1, wherein the type of incontinence event includes a urinary incontinence event, a fecal incontinence event, or a fecal caution event.

3. The incontinence detection system of claim 1, wherein moisture data produced by the moisture detection sensor indicates whether moisture is detected in the incontinence detection pad.

4. The incontinence detection system of claim 1, wherein gas data produced by the gas detection sensor indicates whether the targeted gas is detected in surrounding air near the incontinence detection pad.

5. The incontinence detection system of claim 1, wherein the targeted gas is methane.

6. The incontinence detection system of claim 1, wherein the reader is further configured to determine a level of the targeted gas present in surrounding air.

7. The incontinence detection system of claim 6, wherein
   the reader is further configured to determine whether the level of the targeted gas exceeds a predefined threshold and issue an alert notification in response to a determination that the level of the targeted gas is greater than the predefined threshold, and
   the predefined threshold is based on a level of the targeted gas normally found in the atmosphere.

8. The incontinence detection system of claim 1, wherein the moisture detection sensor is a Radio Frequency Identification (RFID) tag with a plurality of electrodes coupled to the RFID tag.

9. The incontinence detection system of claim 1, wherein the moisture detection sensor is configured to communicate with the reader that evaluates the transmitted signal to determine the status of the incontinence detection pad.

10. The incontinence detection system of claim 9, wherein the reader is an RFID reader.

11. The incontinence detection system of claim 1, wherein the reader is further configured to wirelessly communicate with the server to alert a caregiver of the status of the incontinence detection pad.

12. The incontinence detection system of claim 11, wherein the server is included in a nurse call system.

13. The incontinence detection system of claim 11, wherein the server is included in an electronic medical record (EMR) system.

14. The incontinence detection system of claim 11, wherein the server is configured to communicate with a mobile device of a caregiver.

15. The incontinence detection system of claim 1, wherein the server is configured to communicate with a smart device of a caregiver.

16. The incontinence detection system of claim 11, wherein the reader is further configured to communicate with the server to alert a caregiver of the status of the incontinence detection pad via a wired connection.

17. The incontinence detection system of claim 16, wherein the wired connection comprises a nurse call cable.

18. An incontinence detection system comprising:
   an incontinence detection pad;
   a first moisture detection sensor coupled to the incontinence detection pad and configured to detect a presence of moisture in the incontinence detection pad;
   a second moisture detection sensor coupled to the first moisture detection sensor via a tunnel defined within a fluid impermeable material, the tunnel containing a moisture wicking material; and
   a reader communicatively coupled to the first and second moisture detection sensors to receive moisture data, the reader configured to transmit a signal indicative of a type of incontinence event to a server, and
   wherein the reader is configured to determine a travel time of detected moisture between the first moisture sensor and the second moisture sensor, and the travel time is a time difference between a time at which the first moisture sensor detected a presence of moisture and a time at which the second moisture sensor detected a presence of moisture.

19. The incontinence detection system of claim 18, wherein the first moisture detection sensor is configured to transmit first moisture data to the reader, the second moisture detection sensor is configured to transmit second moisture data to the reader, and the first and second moisture data are indicative of a presence or absence of moisture detected at the corresponding sensor.

20. The incontinence detection system of claim 18, wherein the reader is configured to determine a time between a time at which the first moisture sensor detected a presence of moisture and a time at which the second moisture sensor detected a presence of moisture.

21. The incontinence detection system of claim 1, wherein in determining the type of incontinence event, the reader first determines whether moisture is present based on received moisture data, and, subsequent to determining if moisture is present, determines whether a level of gas exceeds a predetermined threshold to thereby distinguish the type of incontinence event.

22. The incontinence detection system of claim 18, wherein the moisture data is timestamped when transmitted to the reader.

23. The incontinence detection system of claim 18, wherein the reader is configured to (i) compare the travel time with a predefined threshold, and (ii) determine a type of incontinence event based on the travel time between the first and second moisture detection sensors.

24. The incontinence detection system of claim 21, wherein the moisture data is timestamped when transmitted to the reader.

25. The incontinence detection system of claim 21, wherein the incontinence detection pad comprises a rectangular pad situated above the mattress.

* * * * *